United States Patent
Chase et al.

(10) Patent No.: US 6,483,325 B1
(45) Date of Patent: Nov. 19, 2002

(54) MEANS OF CORRECTING A MEASUREMENT OF A PROPERTY OF A MATERIAL WITH A SENSOR THAT IS AFFECTED BY A SECOND PROPERTY OF THE MATERIAL

(75) Inventors: Lee Chase, Los Gatos, CA (US); John D. Goss, San Jose, CA (US); Claud Hagart-Alexander, Vancouver (CA); Martin G. Clarke, N. Vancouver (CA); Graham V. Walford, Oakridge, TN (US); Raymond Yu, Surrey (CA)

(73) Assignee: Honeywell International Inc.

( * ) Notice: Subject to any disclaimer, the term of this patent is extended or adjusted under 35 U.S.C. 154(b) by 34 days.

(21) Appl. No.: 09/594,593

(22) Filed: Jun. 15, 2000

Related U.S. Application Data

(62) Division of application No. 09/289,066, filed on Apr. 12, 1999, now Pat. No. 6,281,689.

(51) Int. Cl.$^7$ ............................................. G01N 27/02
(52) U.S. Cl. ........................ 324/696; 324/449; 162/198
(58) Field of Search ................................. 162/198, 262, 162/263, DIG. 10, DIG. 11; 324/449, 695, 696, 71.1, 663, 441, 447

(56) References Cited

U.S. PATENT DOCUMENTS

| | | | | |
|---|---|---|---|---|
| 3,474,330 A | | 10/1969 | Dauphinee | 162/263 |
| 3,774,238 A | * | 11/1973 | Hardway | 324/663 |
| 4,027,238 A | | 5/1977 | Loch | 324/696 |
| 4,535,285 A | | 8/1985 | Evans et al. | 324/71.1 |
| 4,853,638 A | * | 8/1989 | Endon et al. | 324/441 |
| 5,025,219 A | * | 6/1991 | Gaspard | 324/447 |
| 5,757,197 A | | 5/1998 | O'Neill | 324/695 |
| 5,891,306 A | * | 4/1999 | Chase et al. | 162/198 |
| 5,944,955 A | * | 8/1999 | Bossen et al. | 162/198 |
| 5,954,923 A | | 9/1999 | Chase et al. | 324/449 |

* cited by examiner

Primary Examiner—N. Le
Assistant Examiner—Vincent Q. Nguyen
(74) Attorney, Agent, or Firm—Burns Doane; Anthony Miologos

(57) ABSTRACT

A sensor apparatus and electrode configuration within the sensor apparatus for measuring electrical characteristics of an aqueous fibrous composition. The electrode configuration includes an elongated ground electrode and at least one segmented electrode to form an array of measurement electrode cells. The electrode configuration further includes an array of reference electrode cells formed by a plurality of reference electrodes built into the array of measurement electrode cells. The measurement electrode cells and reference electrode cells have a different sensitivity to water weight of the aqueous fibrous composition and the same sensitivity to conductivity of the aqueous fibrous composition. The measurement apparatus obtains simultaneous resistive measurements from both measurement and reference cells and determines the ratio of the measurements such that the affects from conductivity is canceled out of the measurement ratio. The determined measurement ratio is used to obtain a measurement of the water weight of the aqueous fibrous composition by using previously determined characterization data of the water weight vs. a range of measurement ratios.

9 Claims, 7 Drawing Sheets

MEANS OF CORRECTING A MEASUREMENT OF A PROPERTY OF A MATERIAL WITH A SENSOR THAT IS AFFECTED BY A SECOND PROPERTY OF THE MATERIAL

CROSS-REFERENCE TO RELATED APPLICATIONS

This application is a divisional of Applicants' co-pending application Ser. No. 09/289,066, entitled "MEANS OF CORRECTING A MEASUREMENT OF A PROPERTY FOR A MATERIAL WITH A SENSOR THAT IS AFFECTED BY A SECOND PROPERTY OF THE MATERIAL", filed on Apr. 12, 1999, now U.S. Pat. No. 6,281,689.

BACKGROUND OF THE INVENTION

1. Field of the Invention

The present invention relates to a measurement apparatus utilizing electrodes to measure physical properties of an aqueous fibrous solution, and particularly to a technique of measuring physical properties of wetstock in a sheetmaking machine.

2. State of the Art

In the manufacture of paper on continuous papermaking machines, a web of paper is formed from an aqueous suspension of fibers (wet stock) on a traveling mesh papermaking fabric and water drains by gravity and vacuum suction through the fabric. The web is then transferred to the pressing section where more water is removed by dry felt and pressure. The web next enters the dryer section where steam heated dryers and hot air completes the drying process. The paper machine is essentially a de-watering system. In the sheetmaking art, the term machine direction (MD) refers to the direction that the sheet material travels during the manufacturing process, while the term cross direction (CD) refers to the direction across the width of the sheet which is perpendicular to the machine direction.

In the art of making paper with modern high-speed machines, sheet properties must be continually monitored and controlled to assure sheet quality and to minimize the amount of finished product that is rejected when there is an upset in the manufacturing process. The sheet variables that are most often measured include basis weight, moisture content, and caliper (i.e., thickness) of the sheets at various stages in the manufacturing process. These process variables are typically controlled by, for example, adjusting the feedstock supply rate at the beginning of the process, regulating the amount of steam applied to the paper near the middle of the process, or varying the nip pressure between calendering rollers at the end of the process. Papermaking devices well known in the art are described, for example, in "Handbook for Pulp & Paper Technologists" 2nd ed., G. A. Smook, 1992, Angus Wilde Publications, Inc., and "Pulp and Paper Manufacture" Vol. III (Papermaking and Paperboard Making), R. MacDonald, ed. 1970, McGraw Hill. Sheetmaking systems are further described, for example, in U.S. Pat. Nos. 5,539,634, 5,022,966 4,982,334, 4,786,817, and 4,767,935.

U.S. patent application Ser. No. 08/766,864, now U.S Pat. No. 5,891,306, describes a sensor that measures water weight on the wire of a paper machine. The sensor detects changes in resistance of the wetstock between the electrodes in an electrode array. The resistance of the wetstock between the electrodes is dependent on the amount of water above the electrodes (i.e., the water weight) and the conductivity of the water. Since the conductivity of the water changes from time to time, the resistance measurement does not uniquely determine the amount of water unless some correction for the conductivity is provided. Consequently, the sensor also includes a separate reference cell which is designed to cancel out all affects that change the resistance between the electrodes other than the water weight. For instance, the resistance measurement is affected by changes in conductivity due to changes in the wetstock temperature or chemical composition. The reference cell electrode configuration is designed to have the same configuration as the measurement cell electrode configuration such that they have the same sensitivity to these conductivity changes. In particular, the spacing between electrodes is the same for both the reference cell and the measurement cell. The reference cell is positioned in a container (such as a bucket) outside of the sheetmaking machine having a continuous flow of white water provided from the sheetmaking machine. The white water of a sheetmaking machine is the water that is drained from the wire which is subsequently recycled. The depth of the white water on top of the reference cell in the container is fixed. Because the depth of water above the reference cell is fixed, any resistive changes detected by the reference cell are due to conductivity changes caused by properties other than water weight (i.e., chemical or temperature). Since the reference cell and measurement cells have the same sensitivity to conductivity, the changes in resistance due to changes in conductivity of the reference cell can be converted into a feedback signal which adjusts/compensates the input test signal Vin coupled to the electrode measurement array so that all resistance changes detected by the measurement cells are due to changes in water weight and not in conductivity changes due to chemical or temperature changes.

There are two main problems with this technique. First, the reference sensors within the container become dirty very quickly and give erroneous readings and hence do not provide a feedback signal that correctly compensates the Vin signal. Consequently, the measurement taken by the measurement array can provide erroneous readings. Moreover, the conductivity of the recycled water may be different than the water on the wire being measured. For example, fiber in the wetstock on the wire carries an ionic charge which may cause the water on the wire to be different than the recycled water with little or no fiber. Hence, the compensation or feedback signal provided by the reference cell may not provide an accurate compensation signal.

SUMMARY OF THE INVENTION

The present invention is based in part on the development of a sensor apparatus for measuring electrical characteristics of an aqueous fibrous composition. The apparatus comprises an electrode configuration that is sensitive to at least the following properties of the composition: the conductivity (or resistance), the dielectric constant, and the proximity of the material (e.g., fibrous composition) to the electrode configuration and also comprises a reference electrode configuration. The electrode configuration and measurement apparatus of the present invention includes measurement and reference electrode configurations which allow the sensor apparatus to determine a first property of the aqueous fibrous composition by obtaining resistive measurements corresponding to the first property as well as a second property from both the reference and measurement electrodes.

In one aspect, the invention is directed to a measurement apparatus including at least one measurement electrode cell and a corresponding reference electrode cell. The measurement electrode cell and reference electrode cell have a given sensitivity to a first property of the aqueous fibrous composition and a given sensitivity to a second property of the aqueous fibrous composition. The measurement apparatus obtains simultaneous measurements from both measurement and reference cells. Each of the measurement electrode cell and reference electrode cell have an associated measurement response function to the two properties wherein the resistance (R) measured by each electrode cell is related to the first property (P1) and the second property (P2) as follows: R=f(P1 and P2). Measurement and reference response function equations can be solved using the simultaneously obtained resistance measurements and using previously determined characterization data to determine the first property.

In one embodiment, the response function of each of the measurement and reference electrode cells to the two properties is multiplicative (e.g., R=f1(P1)×f2(P2). The measurement electrode cell and reference electrode cell have a different sensitivity to the first property of the aqueous fibrous composition and the same sensitivity to the second property of the aqueous fibrous composition. In this case, the ratio of the simultaneous measurements obtained from the measurement electrode cell to the reference electrode cell cancels out the affects from the second property. The determined measurement ratio is used to obtain a measurement of the first property of the aqueous fibrous composition by using previously determined characterization data of the first property vs. a range of measurement ratios. In one embodiment, the first property is the water weight of the aqueous composition and the second property is the specific conductivity of the composition. In this case, the measured resistance R, is R=ρ×f(ww)(where ρ=specific resistivity (Ω cm)=1/specific conductivity and f(ww) is a function of the water weight).

In another embodiment, the response of each of the measurement and reference electrode cell to the first and second properties is linearly additive such that R=(A×P1)+ (B×P2) (where A and B are constants and P1 and P2 are measures of the two properties). In this embodiment, the measurement electrode cell and the reference electrode cell are designed to have a different sensitivity to both the first and second properties such that the measurement apparatus is characterized by two linear equations:

$$R_{measured} = AP1+BP2$$

$$R_{reference} = CP1+DP2$$

where $R_{measured}$ and $R_{reference}$ are the measured responses of the two sensors, P1 and P2 are the unknown measures of the two properties, and A, B, C, and D are calibration constants. In order to determine the first property, the two equations are simultaneously solved for P1 and P2 using standard linear algebra techniques and using previously determined characterization data to provide calibration constants A–D.

In one embodiment, the characterization data is obtained off-line. At least one measurement electrode cell is used to take measurements of a sample aqueous fibrous composition so as to obtain characterization data of a range of resistance vs. water depth of the measurement electrode cell. In one embodiment, the off-line measurement electrode cell is designed to have the same sensitivities to the first and second properties of the material as an on-line measurement electrode cell. At least one off-line reference electrode cell having the same sensitivities to the first and second properties as the on-line reference electrode cell is used to take measurements of the sample composition so as to obtain characterization data of a range of resistance vs. water depth of the off-line reference electrode cell. In the case in which the two properties have a multiplicative relationship, the ratio of the two sets of characterization data vs. water weight provides a range of resistive ratios vs. water weight characterization information that is sensitive to water depth but not sensitive to changes in conductivity of the water. The resistive ratio vs. water weight characterization data is then used during on-line measurements. To perform an on-line water weight measurement, simultaneous on-line resistive measurements are obtained from each of the on-line reference and on-line measurement electrode arrays. Next, the water weight is determined by using the determined ratio of the measured resistances and the resistive ratio vs. water weight characterization data.

In one embodiment, a plurality of reference electrode cells are built into the on-line measurement electrode array. The measurement electrode array includes corresponding measurement cells and reference cells. Each cell includes an electrode of which a measurement signal Vin is applied through an impedance element. Each cell further includes a corresponding grounded electrode portion. The separation or spacing between the electrode coupled to the resistive element and the grounded electrode portion determines the sensitivity of the electrode cells to the water depth.

In accordance with the embodiment in which the response of each of the measurement and reference electrode cells to the two properties is multiplicative, the spacing of the measurement electrode cell is different than the spacing of the reference electrode cell such that the measurement and reference electrodes have a different sensitivity to water depth but have the same sensitivity to a second property (e.g., conductivity). In one embodiment, the reference cell has a closer spacing so as to have less of a sensitivity to water weight. In one embodiment, the reference cell electrodes are round. In other embodiments, the reference cell electrodes have other shapes which allow the electrode separation to be different from that of the measurement electrodes.

In one embodiment, the electrode configuration and measurement apparatus of the present invention is used in a sheetmaking system such that the built-in reference cell is effective in correcting for changes in conductivity of wet stock (which are not a result of water weight changes) detected by a measurement cell at the wire of a sheetmaking system. In this embodiment, the ratio of the reference cell resistance to the measurement cell resistance is sensitive to water weight changes (first property) while being insensitive to conductivity (second property) which are not a result of water weight changes.

BRIEF DESCRIPTION OF THE DRAWINGS

The present invention may be further understood from the following written description in conjunction with the appended drawings. In the drawings.

DETAILED DESCRIPTION OF THE PREFERRED EMBODIMENTS

In the following description, numerous specific details are set forth, such as specific electrode spacing or empirical data in order to provide a thorough understanding of the present invention. It will be apparent, however, to one skilled in the art that these specific details need not be employed to practice the present invention. In other instances, well known sheetmaking theory and system components have not been described in order to avoid unnecessarily obscuring the present invention.

Figure 1:
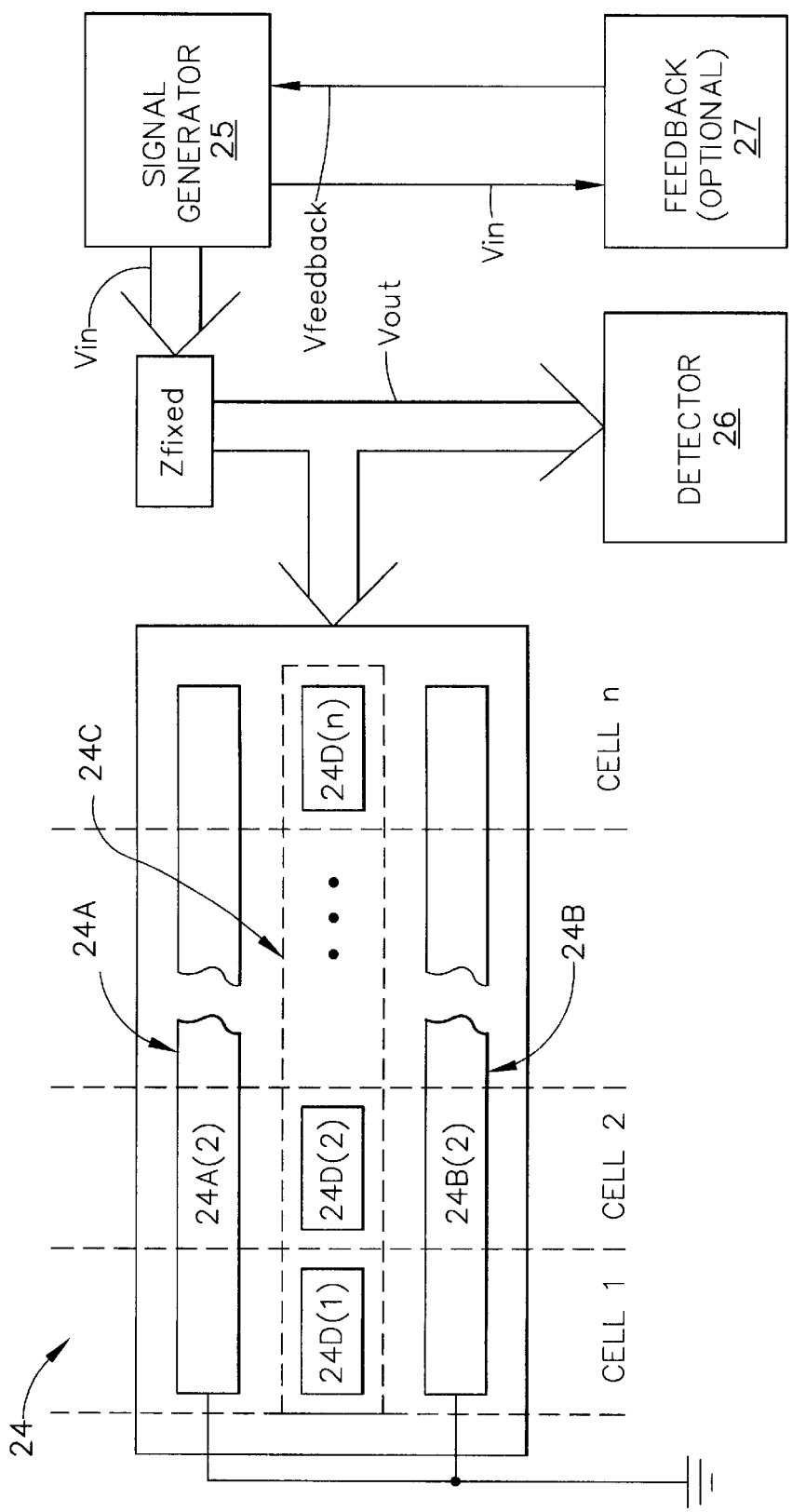
FIG. 1 shows the measurement apparatus as described in U.S. patent application Ser. No. 08/766,864, now U.S. Pat. No. 5,891,306.

FIG. 1 shows a basic embodiment of a conductivity or resistance measurement system, described in U.S. patent application Ser. No. 08/766,864, now U.S. Pat. No. 5,891,306 which is incorporated herein by reference, which detects conductivity or resistance changes of the water in the wetstock material. FIG. 1 shows a sensor array which includes two elongated grounded electrodes 24A and 24B and a segmented electrode 24C. Measurement cells (cell1, cell2, . . . celln) each include a segment of electrode 24C and a corresponding portion of the grounded electrodes (24A and 24B) opposite the segment. Each cell detects a resistance of the wetstock and specifically the water portion of the stock residing in the space between the segment and its corresponding opposing portions of grounded electrode. Each cell is independently coupled to an input measurement voltage (Vin) from signal generator 25 through an impedance element Zfixed and each provides an output voltage to voltage detector 26 on bus Vout. Signal generator 25 provides Vin. Device 26 includes circuitry for detecting variations in voltage from each of the segments in electrodes 24C and any conversion circuitry for converting the voltage variations into useful information relating to the physical characteristics of the aqueous mixture.

Figure 2:
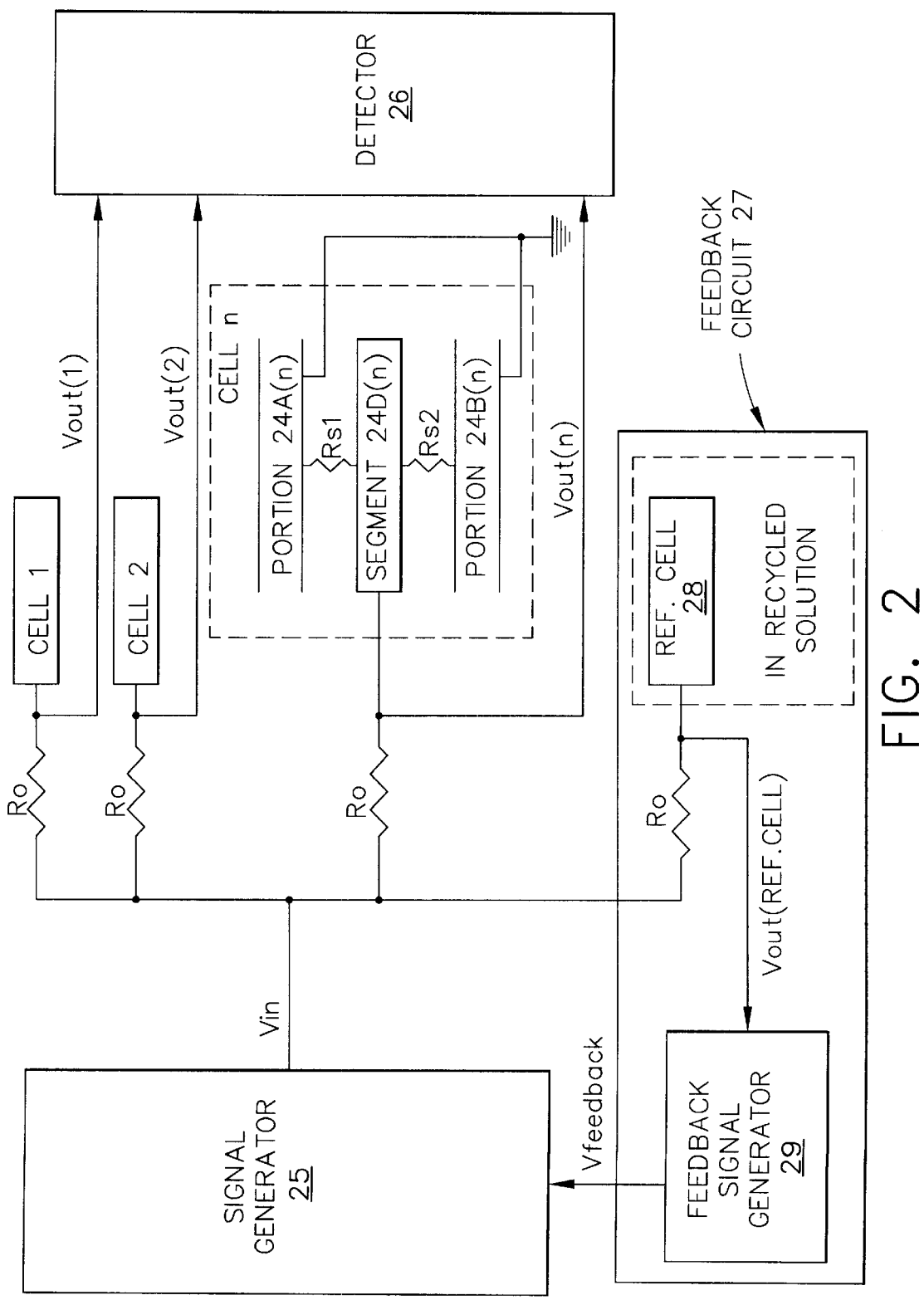
FIG. 2 shows electrical representation of the measurement apparatus shown in FIG. 1.

FIG. 2 illustrates an electrical representation of the measuring apparatus shown in FIG. 1 including cells 1–n of sensor array 24 for measuring conductivity of an aqueous material. As shown, each cell is coupled to Vin from signal generator 25 through an impedance element which, in this embodiment, is resistive element Ro. Referring to cell n, resistor Ro is coupled to center segment 24D(n) and portions 24A(n) and 24B(n) (opposite segment 24D(n)) are coupled to ground. Also shown in FIG. 2 are resistors Rs1 and Rs2 which represent the conductance of the aqueous mixture between the segments and the grounded portions. Resistors Ro, Rs1, and Rs2 form a voltage divider network between Vin and ground. It should be understood that the apparatus shown in FIGS. 1 and 2 can be implemented with a single grounded electrode which is adjacent and positioned opposite to a single segmented electrode.

In the measurement apparatuses shown in FIGS. 1 and 2, resistances Rs1 and Rs2 are dependent on changes in the water depth and the bulk conductivity of the aqueous solution. The bulk conductivity of the solution is dependent on a number of factors which include solution temperature, chemical additions, the amount of fiber, etc. When using the measurement apparatus shown in FIGS. 1 and 2 to measure only water weight, it is necessary to cancel out the affects of the bulk conductivity seen in the detected resistance between the electrodes. One manner in which this is done is to use a feedback apparatus as shown in FIGS. 1 and 2, which generates a feedback signal to adjust Vin to compensate for changes in bulk conductivity.

Figure 3:
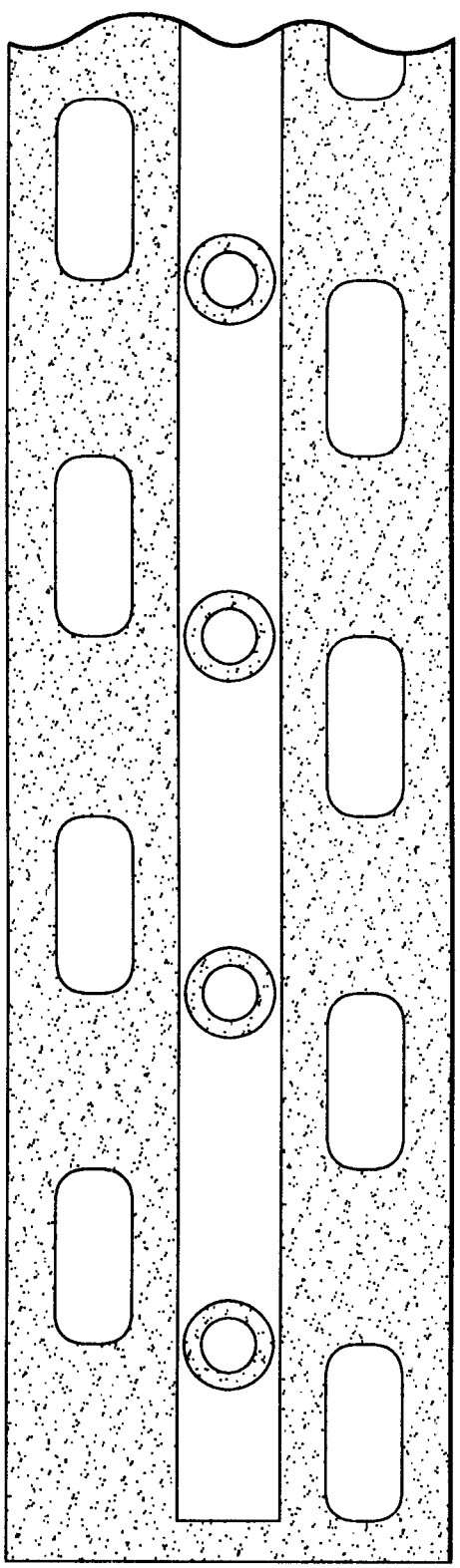
FIG. 3 shows one embodiment of an electrode configuration in accordance with the present invention having a reference cells built into the measurement electrode configuration for use in the measurement apparatus shown in FIG. 1.

The present invention is an electrode configuration for use in the resistive measurement apparatus such as shown in FIGS. 1 and 2. However, instead of using an external reference cell and feedback circuit, the electrode configuration of the present invention includes a built-in reference cell within the measurement electrode configuration. FIG. 3 shows a measurement electrode configuration having a first center elongated grounded electrode and second and third segmented electrodes on either side of the grounded electrode. As with the measurement apparatus shown in FIGS. 1 and 2, each measurement electrode segment is coupled to an impedance element (not shown) which, in turn, is coupled to a measurement input signal. For instance, each measurement electrode segment is coupled to a resistor Ro (as shown in FIG. 2) which is coupled to Vin. An output voltage signal Vout is taken from each electrode segment which corresponds to a detected measurement electrode resistance ($R_{measured}$) of the solution between each electrode segment and ground.

The electrode configuration further includes a plurality of interspaced reference electrodes built into the grounded electrode. The reference electrodes are insulated from (by a circular layer of dielectric), and on top of, the elongated grounded center electrode. The reference electrodes form an array of reference cells each including a reference electrode and the portion of the grounded electrode surrounding the reference electrode. As with the measurement electrodes each reference electrode is coupled to an impedance element and a measurement input signal Vin in order to measure the reference electrode resistance ($R_{ref}$) of the solution between the reference electrode and ground formed by the circle of dielectric encircling the reference electrode. In another embodiment, more than one reference electrode can be associated with a single measurement electrode segment. In still another embodiment, a single segmented electrode can be used instead of two on either side of the ground electrode, wherein the measurement electrode configuration only includes one elongated, segmented electrode and an elongated, grounded electrode.

The relationship of the measurement electrodes and the reference electrodes and the response function of the measurement and reference electrodes to a first and second property form the basic concept of the electrode configuration shown in FIG. 3.

In a first embodiment, the measurement and reference electrodes are constructed so that they have a different sensitivity to a first property but have relatively the same sensitivity to a second property. In one embodiment, both of the reference and measurement electrodes have the same sensitivity to changes in bulk conductivity on the wetstock but have a different sensitivity to changes in water depth. In particular, if the bulk conductivity of the wetstock changes, each of the reference and measurement electrodes detect a similar change in resistance (where water depth is kept constant). However, the reference and measurement electrodes have different sensitivities to changes in water depth. As a result, for the same depth of solution, each of the reference and measurement electrodes will detect a different resistance. Moreover, the response function of the measurement and reference electrodes to the first and second properties is multiplicative, (i.e., $R=f1(P1) \times f2(P2)$), where P1 is a measure of the first property and P2 is a measure of the second property).

The sensitivity of either a reference or measurement electrode cell to the depth of water is dependent on the spacing between the grounded electrode and the electrode opposite the grounded electrode which is coupled to the impedance element. For instance, the spacing between one of the measurement electrode segments and the grounded elongated electrode determines the sensitivity of that measurement cell. Similarly, the space between one of the reference electrodes and the grounded elongated electrode (formed by the dielectric which encircles the reference electrode) determines the sensitivity of the reference cell to water depth.

Figure 4:
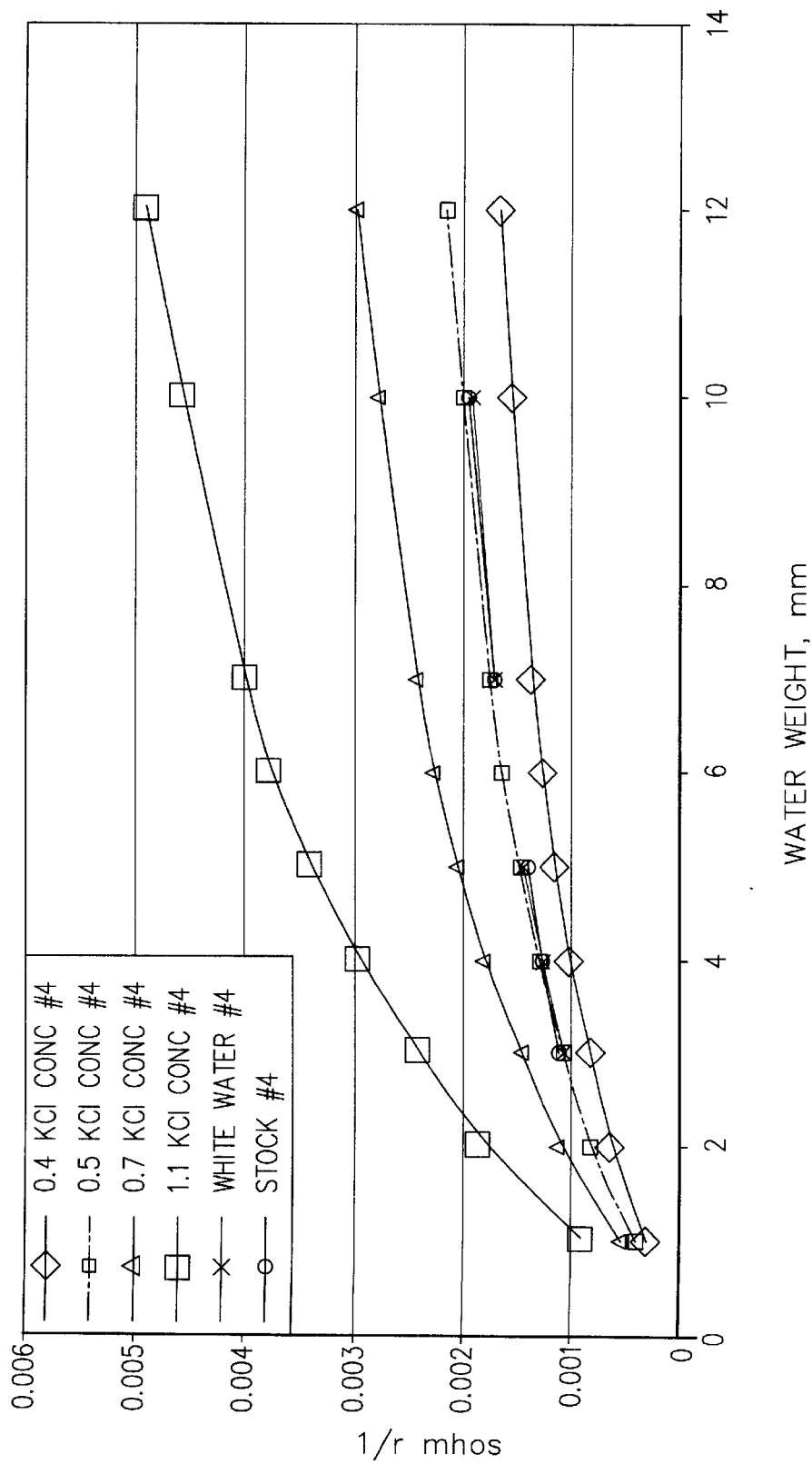
FIG. 4 is a graph showing the high dependency of resistance measurements to bulk conductivity.

FIG. 4 shows a graph illustrating the resistive sensitivity of a measurement cell to the bulk conductivity of a solution. It should be noted that since both of the measurement and reference electrodes exhibit the same resistive sensitivity to the bulk conductivity, a reference cell measurement would result in essentially the same curves shown in FIG. 4. The measurement cell resistance was measured in several solutions of KCl, in water, and wetstock solution. The conductivity of each solution was measured with a lab conductivity meter. The different concentrations of KCl give much different 1/R readings corresponding to the different conductivity. As can be seen in FIG. 4, the resistance is highly dependent on the concentration of the KCl. Since, the KCl concentration corresponds to different bulk conductivities, the resistance is highly dependent on bulk conductivity. One of the basic principles of the first embodiment of the electrode configuration shown in FIG. 3 or a measurement apparatus which includes the first embodiment of the electrode configuration shown in FIG. 3 is to eliminate the affects shown in FIG. 4 of conductivity on water weight measurements taken by the resistive measurement apparatus.

Figure 5:
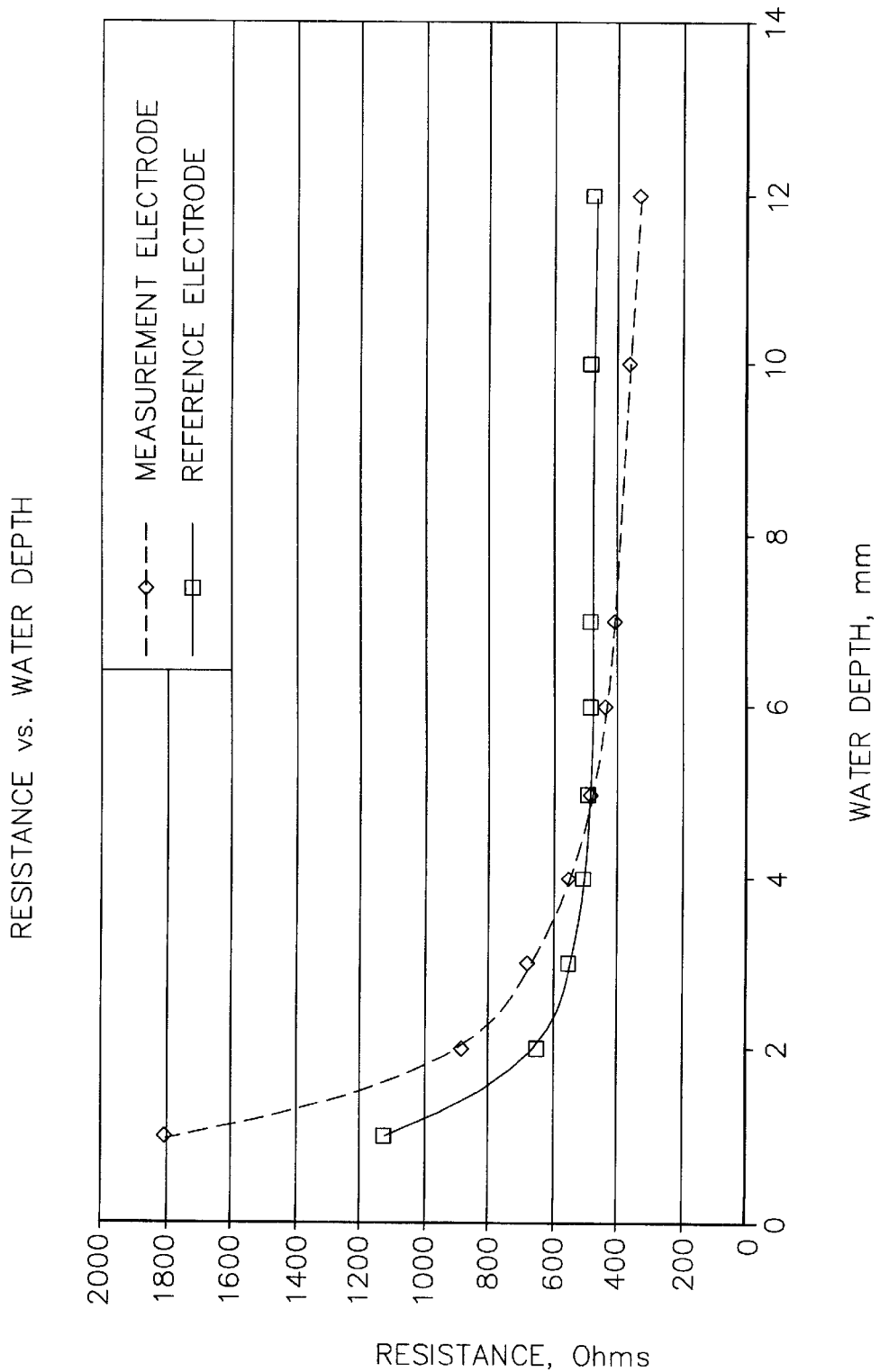
FIG. 5 is a graph showing resistive measurements vs. water depth for each of an off-line reference electrode cell and an off-line measurement electrode cell having different sensitivities to water depth.

FIG. 5 shows a graph of characterization data which illustrates the difference in resistive sensitivity to water depth of each of a reference and a measurement cell each having different electrode spacing. As shown in FIG. 5, the reference cell is much less sensitive to changes in water depth than the measurement cell. This is due to a smaller spacing between the reference electrode and its corresponding grounded electrode.

In one embodiment, the resistive sensitivity vs. water depth characterization data is obtained off-line or outside of the on-line measurement environment by using an electrode configuration such as shown in FIG. 3 which can include either a single measurement cell and a single reference cell or a plurality of measurement and reference cells. The cells are immersed in a solution having a stable bulk conductivity so that the resistance measured by each cell corresponds only to the depth of the water that the electrode configuration is immersed in.

A third graph (shown in FIG. 6), which represents the ratio of the two graphs, is obtained by determining the ratio of the resistance measurement by each of the reference and measurement cells for the same water depth and plotting a range of resistance ratios versus water depth.

The ratio of the resistance measurements essentially cancels out the affects of the bulk conductivity. Specifically, the measurement electrode obtains a resistive measurement according to the following response function:

$$R_{measurement} = f_{measurement}(ww) \times \rho$$

where:

$R_{measurement}$=resistance measured by measurement electrodes, $f_{measurement}(ww)$=response function of resistance to water weight of the measurement electrodes.

This equation follows the general form of the equation ($R=f1(P1) \times f2(P2)$) described previously as follows:

P1=ww=$1^{st}$ property=the water weight in contact with the measurement electrodes, P2=$\rho$=$2^{nd}$ property=the specific resistivity of the water in contact with the measurement electrodes, $f1(P1)=f_{measurement}(ww)$=response function to $1^{st}$ property of measurement electrodes, $f2(P2)=f_{measurement}(\rho)=\rho$=response function to $2^{nd}$ property of measurement electrodes.

Similarly, the reference electrode obtains a resistive measurement according to the following response equation:

$$R_{reference} = f_{reference}(ww) \times \rho$$

where:

$R_{Reference}$=resistance measured by reference electrodes $f_{reference}(ww)$=response function of resistance to water weight of the reference electrodes.

Relating back to the general form of the equation ($R=f1(P1) \times f2(P2)$) described previously, the water properties are the same for the reference electrodes:

P1=ww=$1^{st}$ property=the water weight in contact with the reference electrodes, P2=$\rho$=$2^{nd}$ property=the specific resistivity of the water in contact with the reference electrodes.

The response functions for the reference electrodes are different for water weight but the same for resistivity:

$f1(P1)=f_{reference}(ww)$=response function to $1^{st}$ property of reference electrodes, $f2(P2)=f_{reference}(\rho)=\rho$=response function to $2^{nd}$ property of reference electrodes.

Since the measurement electrode and the reference electrode have the same response to the second property (i.e., $f_{measurement}(\rho)=f_{reference}(\rho)=\rho$), then the ratio of the $R_{measurement}$ to $R_{reference}$ essentially cancels out the effects of the second property.

Figure 6:
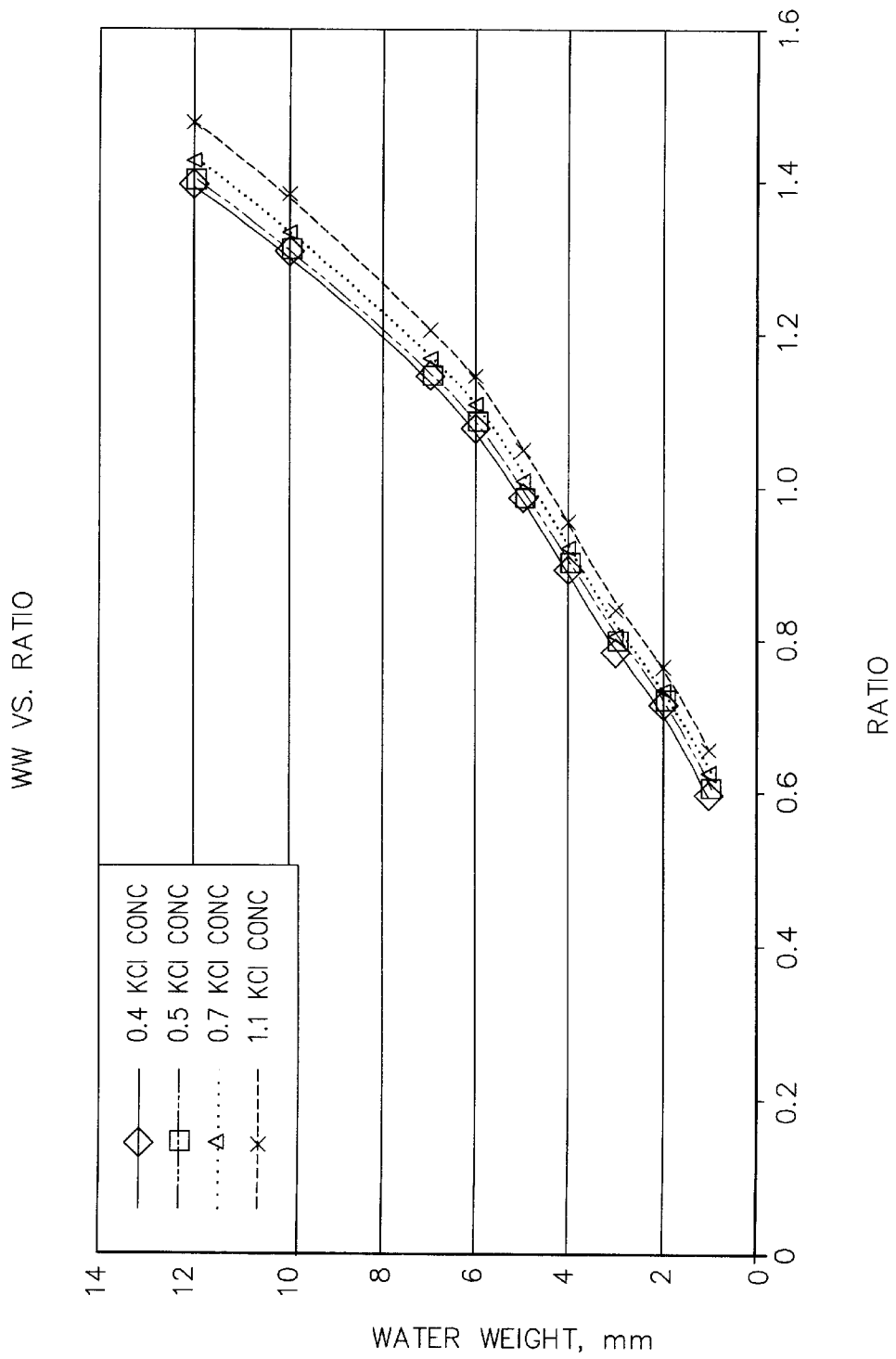
FIG. 6 is a graph showing the ratio of resistance measurements from a reference electrode cell and measurement electrode cell vs. water weight.

FIG. 6 shows several resistance ratios versus water weight curves for several different solutions having different KC1 concentrations which affect bulk conductivity. As shown in FIG. 6, different concentrations have little affect on the ratio curves. Note that the water depth in FIG. 5 has been converted to water weight in FIG. 6. Water depth is easily convertible to water weight wherein 1 mm of water depth= 1000 gm/m$^2$ of water weight.

Figure 7:
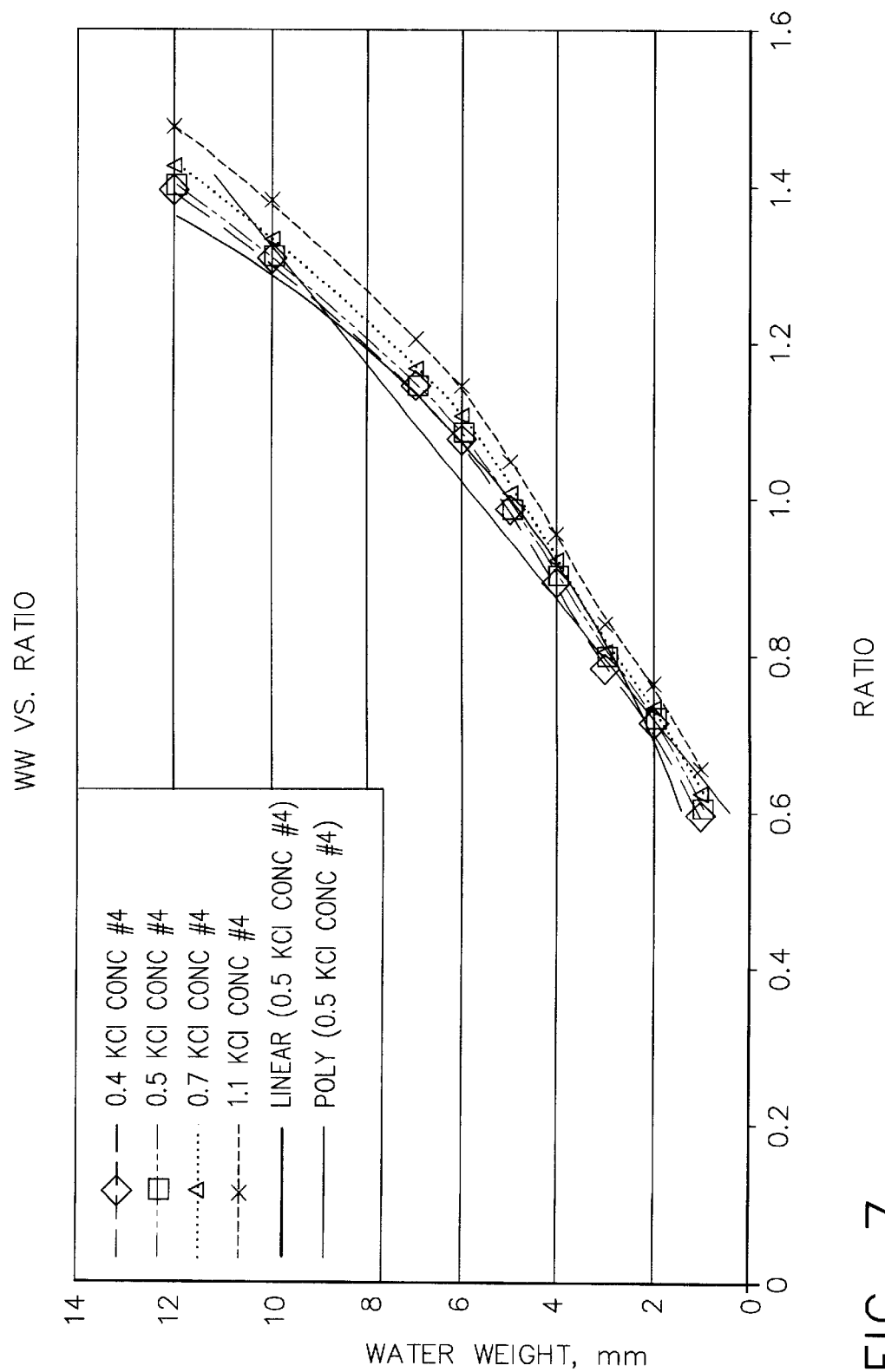
FIG. 7 shows some curve fits to the graphical data shown in FIG. 6.

The results shown in FIG. 6 indicate that a water weight measurement based on the ratio of reference cell to measurement cell resistance holds over a wide range of conductivity changes (i.e., chemical changes) to the white water. FIG. 7 shows curve fits to the graphical data shown in FIG. 6 which facilitates generating an equation for determining water weight given the ratio of the resistive measurements. Curve fitting provides a second order polynomial, with an excellent fit of $R^2=0.9973$ and results in the following equation:

$$y=8.8529x^2-4.3311x+0.5654 \quad (1)$$

where x is the is the ratio and y is the water weight. A simple linear equation gives good fit (i.e., $R^2=0.9741$) over an entire range of water weight from 1000 to 2000 g/m$^2$ and results in the following equation:

$$y=13.467x-7.8175 \quad (2)$$

where x is the is the ratio and y is the water weight. Over the normal range in a paper machine the linear fit is quite adequate and is much simpler to use. Hence, the ratio of the resistive measurements can be obtained using either of these equations by: 1) obtaining resistive measurements from both of the reference and measurement cells, 2) determining the ratio of the measurements, and 3) inserting them into either of the above equations to determine water weight. Alternatively, the graphical data can be converted to look-up table format, which can then be used to determine water weight given the resistive ratio.

Hence, one embodiment of a measurement apparatus including the first embodiment of the electrode configuration shown in FIG. 3 comprises an array of measurement electrode cells and an array of reference electrode cells, each for taking an on-line resistance measurement at essentially the same time. Also included is a means of determining a ratio of resistance measured by each measurement cell and a corresponding reference cell. It should be noted that the corresponding reference cell can be the cell directly across from the measurement cell such that each measurement cell has a corresponding unique reference cell. Alternatively, the same reference cell can be used to provide a resistance measurement for more than one measurement cell. In general, to maintain accurate readings, the reference cell is in the same general vicinity as its corresponding measurement cell so that it is detecting the same water weight. The measurement apparatus further includes a means of using resistive ratios to determine water weight using the previously determined off-line resistive ratio vs. water weight characterization.

In a second embodiment of the electrode configuration shown in FIG. 3, the response of each of the measurement and reference electrodes to the first and second properties is linearly additive such that $R=(A\times P1)+(B\times P2)$ (where A and B are constants and P1 and P2 are measures of the two properties). In this embodiment, the measurement electrode cell and the reference electrode cell are designed to have a different sensitivity to both the first and second properties such that the measurement apparatus including the measurement and reference electrode configurations is characterized by two linear equations:

$$R_{measured}=AP1+BP2$$

$$R_{reference}=CP1+DP2$$

where $R_{measured}$ and $R_{reference}$ are the measured responses of the two sensors, P1 and P2 are the unknown measures of the two properties, and A, B, C, and D are calibration constants. In order to determine the first property, the two equations are simultaneously solved for P1 and P2 using standard linear algebra techniques and using previously determined characterization data to proved calibration constants A–D. Calibration constants can be empirically determined off-line by using an aqueous solution having known first and second properties, measuring the solution resistivity with measurement and reference electrodes to obtain measurement and reference electrode resistivity measurements, and solving the above linear simultaneous equations for the constants.

Hence, another embodiment of a measurement apparatus including the second embodiment of the electrode configuration shown in FIG. 3 comprises an array of measurement electrode cells and an array of reference electrode cells, each for taking an on-line resistance measurement at essentially the same time. Also included is a means of simultaneously solving for the first and second properties using the simultaneous on-line measurements obtained by each of the measurement and reference electrodes and using previously and empirically determined calibration constants.

Finally, it should be noted that other embodiments of electrodes having different sensitivities and response functions not described herein may also be utilized in accordance with the apparatus and method of the present invention.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A sheetmaking system on which a wetstock solution is deposited on a drainage wire, said sheetmaking system including a measurement apparatus for measuring a first property of said wetstock solution on the drainage wire, said measurement apparatus comprising:

a first electrode means having a first associated response function to first and second properties of said wetstock solution wherein the first property is the water weight of the wetstock solution and the second property is the resistance or conductivity of the wetstock solution and having a first sensitivity to said first and second properties, said first electrode means detecting changes in resistance to generate first signals that are indicative of changes in said first and said second properties;

a second electrode means having a second associated response function to said first and second properties of said wetstock solution and having a second sensitivity to said first and said second properties, said second electrode means detecting changes to generate second signals that are indicative of the changes in said first and said second properties, said first and second response functions are each characterized by dependant multiplicative equations and wherein said second electrode means has a different sensitivity to said first property than said first electrode means and has the same sensitivity to said second property as said first electrode means; and means for calculating the water weight of the wetstock using the ratio of said first signals to said second signals and using predetermined characterization data of a range of rations of first signals to second signals versus the water weight of the wetstock.

2. A sheetmaking system on which a wetstock solution is deposited on a drainage wire, said sheetmaking system including a measurement apparatus for measuring a first property of said wetstock solution, said measurement apparatus comprising:

a first electrode means which is sensitive to a first property and a second property of said wetstock solution wherein the first property is the water weight of the wetstock solution and the second property is the resistance or conductivity of the wetstock solution and which detects changes in resistance to generate first signals that are indicative of changes in said first and said second properties;

a second electrode having the same sensitivity to said second property as said first electrode means but having a different sensitivity to said first property as said first electrode, said second electrode means detecting changes in resistance to generate second signals that are indicative of changes in said first and said second properties, said second signals being obtained at essentially the same time as said first signals wherein each of said first and second electrode means has an associated electrode spacing which determines said sensitivity to said first property wherein said associated electrode spacing of said first electrode means is greater than said associated electrode spacing of said second electrode means; and means for calculating the water weight of the wetstock using a ratio of said first signals and said second signals and predetermined characterization data of said first property versus a range of ratios of said first resistive and second resistive measurements.

3. The sheetmaking system of claim 2 wherein:

said first electrode means includes an array of electrode cells, each for generating a first independent signal that is indicative of an independent resistive measurement; and said second electrode means includes an array of electrode cells, each for generating a second signal that is indicative of an independent resistive measurement;

wherein said ratio of said first signals and said second signals comprises a plurality of ratios of said first independent signal from one of said first electrode means electrode cells and a second independent signal from a corresponding one of said second electrode means electrode cell in close proximity to said one of said first electrode cells.

4. The sheetmaking system of claim 2 wherein said first electrode means comprises an elongated grounded electrode and at least one elongated segmented electrode adjacent and opposite to said grounded electrode, and wherein said second electrode means comprises a second segmented elongated electrode including a plurality of inter-spaced electrodes disposed along, on top of, and electrically insulated from said first elongated grounded electrode.

5. The sheetmaking system of 4 wherein said first electrode means includes an array of electrode cells, each for generating a first independent signal wherein each of said first electrode means electrode cells comprise one segment of said at least one elongated segmented electrode and a corresponding adjacent and opposite portion of said grounded electrode; and said second electrode means includes an array of electrode cells for generating a second independent signal, wherein each of said second electrode means electrode cells comprise one of said inter-spaced electrodes and another corresponding adjacent and opposite portion of said grounded electrode;

wherein said ratio of said first signals and said second signals comprises a plurality of ratios of said first independent signal obtained from one of said first electrode means electrode cells and said second independent signal from a corresponding one of said second electrode means electrode cell in close proximity to said one of said first electrode cells.

6. A sheetmaking system on which a wetstock solution is deposited on a drainage wire, said sheetmaking system including a measurement apparatus for measuring a first property of said wetstock solution on the drainage wire, said measurement apparatus comprising:

a first electrode means which is sensitive to a first property and a second property of a wetstock solution wherein the first property is the water weight of the wetstock solution and the second property is the resistance or conductivity of the wetstock solution and which detects changes in resistivity to generate first signals that are indicative of changes in said first and said second properties;

a second electrode means having the same sensitivity to said second property as said first electrode means but having a different sensitivity to said first property as said first electrode, said second electrode means detecting changes in resistivity to generate second signals that are indicative of changes in said first and said second properties, said second signals being generated at essentially the same time as said first signals wherein each of said first and second electrode means has an associated electrode spacing which determines said sensitivity to said first property wherein said associated electrode spacing of said first electrode means is greater than said associated electrode spacing of said second electrode means;

means for determining a ratio of said first signals and said second signals; and means of obtaining a measurement of said water weight of said wetstock solution by using said determined ratio and predetermined characterization data of said first property versus a range of ratios of said first and second measurements.

7. The sheetmaking system of claim 6 wherein:

said first electrode means includes an array of electrode cells, each for generating a first independent signal; and said second electrode means includes an array of electrode cells, each for generating a second independent signal;

wherein said ratio of said first signals and said second signals comprises a plurality of ratios of said first independent signal obtained from one of said first electrode means electrode cells and a second independent signal from a corresponding one of said second electrode means electrode cell in close proximity to said one of said first electrode cells.

8. The sheetmaking system of claim 6 wherein said first electrode means comprises an elongated grounded electrode and at least one elongated segmented electrode adjacent and opposite to said grounded electrode, and wherein said second electrode means comprises a second segmented elongated electrode including a plurality of inter-spaced electrodes disposed along, on top of, and electrically insulated from said first elongated grounded electrode.

9. The sheetmaking system of claim 8, wherein said first electrode means includes an array of electrode cells, each for generating a first independent signal wherein each of said first electrode means electrode cells comprise one segment of said at least one elongated segmented electrode and a corresponding adjacent and opposite portion of said grounded electrode; and said second electrode means includes an array of electrode cells, each for generating a second independent resistive measurement wherein each of said second electrode means electrode cells comprise one of said inter-spaced electrodes and another corresponding adjacent and opposite portion of said grounded electrode;

wherein said ratio of said first independent signal from one of said first electrode means electrode cells and said second signal obtained from a corresponding one of said second electrode means electrode cell in close proximity to said one of said first electrode cells.

* * * * *